United States Patent [19]

De Mey et al.

[11] 4,420,558
[45] Dec. 13, 1983

[54] BRIGHT FIELD LIGHT MICROSCOPIC METHOD OF ENUMERATING AND CHARACTERIZING SUBTYPES OF WHITE BLOOD CELLS AND THEIR PRECURSORS

[75] Inventors: Jan R. De Mey, Turnhout; Marc K. J. J. Moeremans, Mol, both of Belgium

[73] Assignee: Janssen Pharmaceutica N.V., Beerse, Belgium

[21] Appl. No.: 316,204

[22] Filed: Oct. 29, 1981

Related U.S. Application Data

[63] Continuation-in-part of Ser. No. 233,809, Feb. 12, 1981, abandoned.

[51] Int. Cl.³ ............... G01N 33/48; G01N 33/52; G01N 33/54
[52] U.S. Cl. ............................. 435/7; 424/3; 435/4; 435/28; 436/63; 436/519
[58] Field of Search ............... 23/230 B; 424/12, 3; 435/4, 7, 28; 436/519, 63

[56] References Cited

U.S. PATENT DOCUMENTS

| | | | |
|---|---|---|---|
| 3,916,205 | 10/1975 | Kleinerman | 424/3 X |
| 3,988,115 | 10/1976 | Modabber | 436/519 X |
| 4,146,604 | 3/1979 | Kleinerman | 424/3 |
| 4,148,870 | 4/1979 | Hydes | 424/3 |
| 4,223,005 | 9/1980 | Teodorescu | 424/3 X |
| 4,225,783 | 9/1980 | Palin | 424/3 X |
| 4,313,734 | 2/1982 | Leuvering | 436/525 |

OTHER PUBLICATIONS

J. Roth et al., J. Histochem., Cytochem., 25, 1181–1184, (1977).
M. Horisberger et al., Experientia, 51, 1147–1149, (1975).
W. D. Geoghegan et al., Immunol. Commun. 70, 1–12, (1978).
W. D. Geoghegan, et al., J. Histoch. Cytochem., 25 (11), 1187–1200, (1977).
"Gradwohl's", Sam Frankel et al., eds., vol. 1, 510, 511, C. V. Mosby Co., Saint Louis, 1970.

*Primary Examiner*—Sidney Marantz
*Attorney, Agent, or Firm*—Geoffrey G. Dellenbaugh

[57] ABSTRACT

A bright field light microscopic method for enumerating and characterizing subtypes of white blood cells and their precursors. The cells are labelled either directly or indirectly with gold-labelled antibodies in the presence of an inhibitor of oxidative phosphorylation.

19 Claims, No Drawings

BRIGHT FIELD LIGHT MICROSCOPIC METHOD OF ENUMERATING AND CHARACTERIZING SUBTYPES OF WHITE BLOOD CELLS AND THEIR PRECURSORS

CROSS-REFERENCE TO RELATED APPLICATIONS

This is a continuation-in-part of our copending application Ser. No. 233,809, filed Feb. 12, 1981, now abandoned.

DESCRIPTION OF THE INVENTION

This invention is concerned with a bright field light microscopic method for enumerating and characterizing subtypes of white blood cells and their precursors by labeling the latter, either directly with gold-labeled antibodies or indirectly with antibodies and gold-labeled secondary antibodies. A particularly important feature of the subject invention is that it provides an inexpensive, convenient and reliable routine method of selectively counting and defining subpopulations of B- and T-lymphocytes, by the use of highly specific antibodies to differentiate surface antigens.

Counting subpopulations of lymphocytes has both scientific and clinical importance, in view of their role in immunological host defense mechanisms, and diseases involving the immunological system. The immune response comprises both cellular immunity and humoral immunity, the latter involving antibody formation. These two types of responses have their origin in two distinct populations of lymphocytes: the T- and B-cells respectively. Lymphocytes are cells, equipped to specifically recognize and respond to antigens. B- and T-cells begin their development in the bone marrow. B-cells migrate to the avian Bursa of Fabricius where they differentiate into mature cells. The site of B-cell differentiation in mammals is unknown. The immature T-cells, or prothymocytes, migrate to the thymus, wherein they differentiate into thymocytes. The B- and T-cell populations interact in the immune system as a balanced partnership and immunization can be visualized as a process in which an antigenic trigger perturbs the system and moves it to a new point of equilibrium. Humoral immunity is elicited by a cooperation of B- and T-cells. B-cells are transformed in antibody secreting plasma cells. T-cells, have at least three main functions in both humoral and cellular immunity: (1) cytotoxicity, whereby they destroy host cells bearing abnormal antigens; (2) inducer (helper) activity that induces a number of effector functions, including T-lymphocyte cytotoxicity and B-lymphocyte production of antibody; (3) suppression, whereby the two former functions are attenuated.

The several functions of T-cells are not expressed at the same time by all T-lymphocytes. Each function is performed by a subclass of T-lymphocytes programmed for that function. Functionally distinct T-lymphocyte subclasses are generated by the developmental process of divergent and sequential differentiative steps connoting discrete genetic programs.

Most importantly now, it has been shown that the genetic programs of each T-lymphocyte subset dictates not only its assigned function but also the expression of particular molecules on the cell surface (the "surface phenotype") which allocate the cell with different cell-surface characteristics and allow them to react with different markers. Membrane surface markers can be divided in three general categories, i.e., receptors, erythrocyte rosettes and antigens. Receptors can be detected by their ability to bind specific ligands such as IgG, complement $C_3d$ or IgM.

Erythrocytes from several non-human species are able to bind certain human lymphocyte types, forming rosettes. For example, sheep erythrocytes, at 0° C., spontaneously form rosettes with human T-cells, while mouse erythrocytes bind exclusively to human B-cells. Surface antigens can be demonstrated with specific antibodies. Until recently (see below), this was only possible to a very limited extent for human cells because such antibodies were not generally available. The ability to define, distinguish and isolate human white blood cells, and particularly T-cell subclasses would be of inestimable value in many aspects of clinical immunology. This was virtually impracticable until the advent of hybridoma technology, which now makes it feasable to produce the range of antibodies necessary to define their developmental rank and function. Clones producing such monoclonal antibodies have now been described in Science, 206: 347–349 (1979); J. Immunol., 123: 1312–1318 (1979); J. Immunol., 123: 2894–2986 (1979); J. Immunol., 124: 1301–1307 (1980).

These monoclonal reagents have already progressed to the point of clinical utility. In normal subjects, about 70–80% of the blood lymphocytes are T-cells. About 50% are helper/inducer cells and about 25% supressor/cytotoxic cells. Loss or activation of these subsets leads to an imbalance, resulting in immunologic disorders such as auto-immunity or immunodeficiency. For example, increased counts of activated suppressor cells have been found after viral infections such as infectious mononucleosis. This may account for the transient immunologic hyporesponsiveness observed after such viral infections. It has also been shown (Proc. Natl. Acad. Sci., 77: 1588–1592, 1980) that these monoclonal reagents are useful in the diagnosis and classification of T-lymphocyte acute lymphatic leukemia and that this classification may have prognostic and therapeutic significance. In view of the above, it will be evident that the routine quantitative determination and definition of T- and B-lymphocytes and their subpopulations, as well as other white blood cell types is extremely useful for both diagnostic and research purposes. Such methods indeed (1) provide a measure of the immunoregulatory status of a given individual, (2) are invaluable for the classification and diagnosis of white blood cell neoplasms and (3) prove useful in monitoring the response of patients to treatment.

In the prior art, indirect immunofluorescence techniques, in combination with fluorescence microscopy or automated cytofluorography have been used. While being relatively simple as a technique, immunofluorescence is difficult to quantitate, unless in the hands of very skilled persons.

The major problem is concerned with the fading of fluorescence, making it difficult to see weakly positive cells. On the other hand, cytofluorography is still to expensive for routine large-scale use. Techniques using enzyme conjugates have been developed.

In spite of their advantages, they are still very demanding in terms of the production of high-quality enzyme-labeled reagents. A further disadvantage of enzyme-labeled reagents is that they necessitate an additional reactin to visualize the immuno-labeled cells.

Thus, although potentially useful, they would not allow their use on a routine large-scale basis.

In Immunol. Commun., 7, 1(1978), it is shown that colloidal gold granules, coated with the IgG factor of rabbit anti-goat/IgG can be used for the indirect light microscopic detection of surface immunoglobulines at the surface of B-lymphocytes, using goat anti-human IgD and IgM. The method was applied to cells that had been isolated by the Ficoll Hypaque method, and fixed with glutaraldehyde. In order to observe capping, fixation was also done after incubating the cells with the antibodies against surface immunoglobulins at 37° C. and before incubating them with the gold-labeled antibodies. Although the method proves satisfactory for the detection of cell surface immunoglobulins, it has been found inadequate (as will be shown below) for the light microscopic detection of cell-surface differentiation antigens.

In view however, of the possible advantages of gold as a light microscopic marker, we have further explored its applicability for use with the monoclonal reagents, and have discovered a satisfactory procedure which will be described below. Cell surface differentiation antigens are much less abundant than surface immunoglobulins on B-cells, and are much more difficult to detect, also by classical immunofluorescence techniques. It has been shown experimentally that whenever pre-fixed cells are allowed to react with gold-labeled antibodies to less abundant cell-surface differentiation antigens, the contrast of the label is not sufficient for reliable bright field light microscopic examination. Likewise, incubation of living cells with such primary antibodies, followed by fixation and subsequent incubation with gold-labeled secondary antibodies did not produce reliable results. In addition, for the indirect method it was found necessary to coat the granules with affinity-purified secondary antibodies, since the γ-globulin fraction of the same antiserum, linked to the gold granules was completely uneffective.

According to the present invention, it has been discovered that a clear labeling of cell-surface differentiation antigens can be achieved by applying the complete immuno-gold-staining method to viable cells, which are, until fixation, kept in contact of an appropriate inhibitor of oxidative phosphorylation. The inhibitor of oxidative phosphorylation blocks all active processes such as capping and all forms of non-specific and specific internalization of the gold antibodies. It allows however extensive patching of specifically bound ligands, and this patching, as has been checked with electron microscopy, provides one of the bases for the present invention, because: (1) the patches are clearly visible in the bright field light microscope, and are evenly distributed over the cell surface. This allows to formulate very clear-cut criteria for evaluation of positiveness; (2) the absence of internalization of the gold particles provides the necessary specificity.

It was also discovered that non-specific binding of the gold label itself to certain cells, could be inhibited with the use of 2% human plasma in all buffers and reagents.

As a result of the highly increased sensitivity which is obtained in this way, there is provided by the present invention a new, simple, bright field light microscopic method of enumerating and typing populations of white blood cells, including their precursors, occurring in blood, bone marrow or lymphoid organs. Thus, in principle, cells isolated from any source can be used. The method may also be applied to whole blood. As stated in Scand. J. Immunol., 3, 161, (1974), methods for the accurate enumeration of circulating lymphocyte populations should avoid cell separation procedures. In the concerned reference, it is shown that such methods give subtotal yields and may distort the ratio between different white blood cell populations. In the present method, prior art methods for the detection of cells containing endogenous peroxidase-activity are used, to eliminate the PMN's and monocytes from the counts.

Cells possessing this activity are easily coloured by contacting them with peroxidase markers, such as 3,3'-diaminobenzidine (DAB) or a mixture of p-phenylene diamine and pyrocatechol, known as Hanker Yates reagent.

The use of the Hanker Yates reagent has not been reported before and presents an interesting alternative in view of the carcinogenicity of DAB. The advantages of the prsesent method are multiple. The procedure is straight forward end reproducible.

The clear-cut criteria of positiveness makes it suitable for routine clinical use, without the need of sophisticated equipment, and it easily lends itself to automation. The method may be carried out on whole blood, thus avoiding time consuming cell separations. Since colloidal gold is a stain by itself there is no need for a further reaction. The procedure gives stable preparations and is not expensive. The gold labeled antibodies, taken appropriately prepared, are stable and can be stored for several months with minimal leakage of protein from the gold. The direct labeling method according to the invention allows for multiple labeling to detect possible overlapping distributions by ultramicroscopical examination.

As stated above, the present method can be applied to whole blood, which constitutes a considerable advantage in comparison with other techniques which require sophisticated separations and/or cell sorting. However, it has been found that in most cases, it may be advantageous to lyse the erythrocytes by contacting them with an ammonium chloride solution (Proc. Natl. Acad. Sci., 77: 4914–4917, 1980). This yields a highly enriched white blood cell population without introducing a separation step. In principle, the method can be used to determine any type of circulating blood cells and their precursors, such as, for example, erythrocytes, polymorphonulear cells, platelets, monocytes, plasma cells, B-lymphocytes and T-lymphocytes, as well as subpopulations thereof. However, in view of the availability of rather simple counting techniques for certain of these cell types, such as erythrocytes, PMN's and platelets, the advantages of the present invention are in practice most relevant for the quantitative and qualitative determination of T- and B-lymphocytes and their subpopulations and for the determination of monocytes.

The process of the present invention is carried out as follows. One drop of a suitably prepared cell suspension, obtained from whole blood or after a separation technique, (for example in the case of non-circulating cells), containing at least about 95% viable cells is incubated with a specific antibody in an appropriate medium. The cells are washed with an appropriate washing medium and, in case gold-labeled primary antibodies are used, the cells are thereafter subject to fixation. Otherwise they are incubated with gold-labeled secondary antibodies and after repeated washings they are fixed. The fixed cells are washed again, a smear is made and after air drying the cells are fixed a second time. In case peroxidase containing cells are to be distinguished, those are coloured by contacting them with an appropriate peroxidase-indicator. The cells are washed, counterstained, dehydrated and mounted in an appropriate mounting medium. It is an essential requirement of the method according to the invention that the incubation with the antibodies, and all steps up to fixation of the cells are carried out on viable cells in the presence of a sufficient concentration of an inhibitor of oxydative phosphorylation to allow for extensive patching and prevent capping and all forms of internalization of the gold-labeled antibodies. For this purpose, there is preferably made use of an alkalimetal azide, such as sodium azide in a concentration of about 0.02 M. Apart from sodium azide the incubation and washing mediums will usually comprise buffered saline, preferably phosphate buffered saline pH 7.2, which further comprises about 1% of bovine serum albumin. In case whole blood is used, it is often advantageous to enrich the white blood cells by lysing the erythrocytes by contacting them for a sufficient time, usually about 5 minutes, with a 0.9% ammonium chloride solution. The first fixation of the cells is advantageously done with 0.01–0.1% glutaraldehyde: this enhances the detectability of the endogenous peroxidase containing cells. The second fixation may be done for example with formaldehyde and ethanol. This serves to fix the cells firmly to the glass slide. As a peroxidase indicator, there may be used 3,3'-diaminobenzidine (DAB) or a mixture of p-phenylene diamine and pyrocatechol known as Hanker-Yates reagent. Counterstaining of the cells may be done with methyl green and the subsequent dehydratation may be achieved by using, for example, ethanol and xylene. Appropriate mounting media, usually resins, are readily available.

The preparation is subsequently subject to light microscopic examination wherein the positive cells are distinguished from the negative cells by the presence at their surface of evenly distributed dot-like, red-blue granules. Due to the new preparation technique, the nucleated cells show some shrinkage and this is probably helpful for concentrating the gold at the surface in a more aggregated state.

The results with indirect labeling seem to be somewhat more reliable than with the direct method. The latter method may however, find special utility in multiple labeling ultrastructural studies with different antibodies, adsorbed to gold particles of difference sizes.

The specific antibodies used in the present method are available or can be obtained by methodologies known in the art. For example, monoclonal mouse antibodies to peripheral lymphocytes and the to the helper and suppressor cell subpopulations have been described in Science, 206: 347 (1979) and are available through Ortho Diagnostics, Raritan, N.J. (U.S.A.), under the name Orthoclone. When using these primary monoclonal mouse antibodies, secondary antibodies may be, for example, of the type goat-anti-mouse IgG.

For gold-labeling of antibodies, we have modified on essential points art-known methodologies, as described, for example in J. Histoch. Cytochem., 25: 1187 (1977), and Experientia, 51: 1147 (1975).

Said modification consists essentially herein that (1) prior to coupling, the antibodies were dialyzed against a 2 mM borax buffer of pH 9 instead of against distilled water or unbuffered 0.005 M NaCl. (2) BSA, dialysed against 2 mM borax buffer on pH 9 was used instead of PEG 20 000 to prevent aggregation of the gold preparations and (3) Tris/Saline buffer, pH 8.2 containing 1% BSA is used for washing and storing the gold-labeled antibodies. Using this new procedure and exclusively affinity purified antibodies, extremely stable and highly active preparations were obtained. For light microscopy, 20 nm gold particles were found to present the minimal size and 40 nm gold was found to give optimal results.

The invention is further illustrated by the following examples which are not intended to limit but to exemplify the scope thereof.

EXAMPLE I

Determination of T-lymphocytes in whole human blood by the indirect method

A. Preparation of colloidal-gold labelled antibodies

Goat anti-mouse/IgG antibodies were purified from antiserum by affinity-chromatography. Purified antibodies are dialyzed overnight at 4° C. at about 1 g/l against 2 mM borax buffer of pH 9. They are then centrifuged for 1 hour at 100 000 g at 4° C. and the upper ⅔ layer is used the same day. An appropriate amount of gold sol of 18–20 nm or 40 nm diameter prepared by the method of Frens (Nature, Phys. Sci., 241: 20, 1973) is adjusted to pH 9.0 with $K_2CO_3$. To this sol is added dropwise, but quickly, the antibody solution. About 1 mg of antibody in 1 ml is added to 100 ml of the gold sol.

After gentle stirring for 1 min at room temperature there is added 10 ml of a 10% BSA solution, dialysed against the 2 mM borax buffer pH 9.0. Unbound proteins are removed by three cycles of centrifugation and resuspension in BSA buffer (20 mM Tris buffered saline pH 8.2+10 mg/ml BSA). The final pool formed at the bottom of the centrifuge tube is finally taken up in about 10 ml of 1% BSA buffer+0.02 M $NaN_3$.

B. Determination of T-lymphocytes in whole human blood.

To 0.5 ml of EDTA (=ethylene diamine tetraacetate)-anticoagulated blood are added 5 ml of a lysis buffer of pH 7.3 comprising 8.29 g/l of $NH_4Cl$, 0.037 g/l of $Na_2$-EDTA, 1.0 g/l of $KHCO_3$. The leukocytes are collected by centrifugation at 1500 rpm during 5 minutes and washed in phosphate-buffered saline of pH 7.2 comprising 1% of bovine serum albumin (BSA) and $2.10^{-2}$ M of sodium azide (BSA-buffer). Finally the cells are resuspended in one drop (about 25 μl) of phosphate buffered saline of pH 7.2 comprising 5% of BSA, 2% human plasma, and $2.10^{-2}$ M of sodium azide and 25 μl of appropriately diluted monoclonal mouse antibodies to human T-lymphocytes (Orthoclone—OKT 3, QAN) are added (dilution made up in BSA/Azide/PBS+2% human plasma). The cells are incubated for 30 minutes at room temperature and thereafter the non-reacted antibodies are removed by 3 cycles of resuspension of the cells in 2 ml of BSA buffer consisting of phosphate-buffered saline of pH 7.2 comprising 1% of BSA, 2% human plasma, and $2.10^{-2}$ M of sodium azide, and centrifugation at 1500 rpm for 5 minutes.

The cells are resuspended in 25 μl of 2% human plasma supplemented gold-labeled GAM (goat-antimous) antibodies, and the cells are incubated for 60 minutes at room temperature.

The non-reacted antibodies are removed by 3 cycles of resuspension and centrifugation in BSA buffer as described above. The cells are resuspended in 2 ml of a fixative comprising 0.01–0.1% of glutaraldehyde in phosphate buffered saline and incubated for 10 minutes. They are subsequently washed in PBS and a smear is made. After air-drying the cells are post-fixed with 10% formaldehyde in ethanol for 2 minutes and washed in water. In order to detect cells with endogenous peroxidase activity the cells are contacted with a solution of 0.5 mg/ml of Hanker Yates reagent in a 100 mM Tris-buffer of pH 7.6, comprising further 0.001% of hydrogen peroxide for 10 min.

The preparations are washed with water and air-dried. They are counter-stained with 1% of chloroform-extracted methyl green in water during 2 minutes, rinsed shortly in water and dehydrated by serial treatment with ethanol and xylene.

Positive cells have clearly visible dark granules, evenly distributed over the cell surface.

The gold-labeled peroxidase-negative cells versus unlabeled peroxidase negative cells are counted under the light microscope at magnifications from 500 on with immersion oil lenses and correspond with the T-lymphocyte population.

EXAMPLE II

Determination of helper/inducer T-lymphocytes in whole blood by the direct method.

A. Determination of helper/inducer T-lymphocytes

From one drop of whole blood, the erythrocytes are removed as described in example I and the remaining cells are suspended in one drop of the gold-labeled antibodies to human T-lymphocytes supplemented with 2% human plasma described above and the procedure of example I, from the washing and fixation in 0.01–0.1% gluteraldehyde is further repeated.

The gold-labeled peroxidase-negative cells, which are counted versus unlabeled peroxidase negative cells under the light microscpe correspond with the helper/inducer subpopulation of human T-lymphocytes.

What is claimed is:

1. A bright field light microscopic ethod for the quantitative determination and characterization of white blood cells and precursors thereof, which comprises the steps of
   (i) labeling viable cells of the desired subtype by allowing them to react first with specific non-labeled antibodies and thereafter with appropriate gold-labeled secondary antibodies, whereby the cells are, until fixation, allowed to undergo extensive patching of the antigens, but are prevented from capping and all forms of internalization by keeping them in contact with an effective concentration of an appropriate inhibitor of oxidative phosphorylation;
   (ii) fixing the cells and staining the cells with endogenous peroxidase activity by contacting them with an appropriate peroxidase-indicator; and
   (iii) counting and identifying the gold-labeled cells in a given sample under the bright field light microscope.

2. A bright field light microscopic method for the quantitative determination and characterization of white blood cells and their precursors, comprising the steps of
   (i) labeling viable cells of the desired subtype by allowing them to react with specific gold-labeled antibodies, whereby the cells are, until fixation, allowed to undergo extensive patching of the antigens, but are prevented from capping and all forms of internalization by keeping them in contact with an effective concentration of an appropriate inhibitor of oxidative phosphorylation;
   (ii) fixing the cells and staining the cells with endogenous peroxidase activity by contacting them with an appropriate peroxidase-indicator; and
   (iii) counting and identifying the gold-labeled cells in a given sample under the bright field light microscope.

3. A bright field light microscopic method for the quantitative determination and characterization of subtypes of white blood cells and their precursors, comprising the steps of
   (i) allowing viable cells of the desired subtype to react with specific non-labeled antibodies;
   (ii) labeling the thus formed complexes by allowing them to react with appropriate gold-labeled secondary antibodies, whereby the cells are, until fixation, allowed to undergo extensive patching of the antigens, but are prevented from capping and all forms of internalization by keeping them in contact with an effective concentration of an appropriate inhibitor of oxidative phosphorylation;
   (iii) fixing the cells and staining the cells with endogenous peroxidase activity by contacting them with an appropriate peroxidase-indicator; and
   (iv) counting and identifying the gold-labeled cells in a given sample under the bright field light microscope.

4. A bright field light microscopic method for the quantitative determination and characterization of human T-lymphocytes which comprises the steps of
   (i) labeling said human T-lymphocytes by allowing them to react, in a viable state, with gold-labeled antibodies to human T-lymphocytes, whereby the cells are, until fixation, allowed to undergo extensive patching of the antigens, but are prevented from capping and all forms of internalization by keeping them in contact with an effective concentration of an appropriate inhibitor of oxidative phosphorylation;
   (ii) fixing the cells and staining the cells with endogenous peroxidase activity by contacting them with an appropriate peroxidase-indicator; and
   (iii) counting the peroxidase-negative gold-labeled cells in a given sample under the light microscope.

5. A bright field light microscopic method for the quantitative determination and characterization of human T-lymphocytes which comprises the steps of
   (i) allowing said human T-lymphocytes to react, in a viable state, with non-labeled antibodies to human T-lymphocytes;
   (ii) labeling the thus formed complexes by allowing them to react with appropriate gold-labeled secondary antibodies, whereby the cells are, until fixation, allowed to undergo extensive patching of the antigens, but are prevented from capping and all forms of internalization by keeping them in contact with an effective concentration of an appropriate inhibitor of oxidative phosphorylation;
   (iii) fixing the cells and staining the cells with endogenous peroxidase activity by contacting them with an appropriate peroxidase indicator; and
   (iv) counting the peroxidase-negative gold-labeled cells in a given sample under the light microscope.

6. A bright field light microscopic method for the quantitative determination of a subpopulation of human T-lymphocytes which comprises the steps of
   (i) labeling the cells of said subpopulation by allowing them to react, in a viable state, with gold-labeled antibodies to said subpopulation, whereby the cells are, until fixation, allowed to undergo extensive patching of the antigens, but are prevented from capping and all forms of internalization by keeping them in contact with an effective concentration of an appropriate inhibitor of oxidative phosphorylation;

(ii) fixing the cells and staining the cells with endogenous peroxidase activity by contacting them with an appropriate peroxidase indicator; and (iii) counting the peroxidase-negative gold-labeled cells in a given sample under the light microscope.

7. A bright field light microscopic method for the quantitative determination of a subpopulation of human T-lymphocytes which comprises the steps of (i) allowing the cells of said subpopulation to react, in a viable state, with non-labeled antibodies to said subpopulation;

(ii) labeling the thus formed complexes by allowing them to react with appropriate gold-labeled secondary antibodies, whereby the cells are, until fixation, allowed to undergo extensive patching of the antigens, but are prevented from capping and all forms of internalization by keeping them in contact with an effective concentration of an appropriate inhibitor of oxidative phosphorylation;

(iii) fixing the cells and staining the cells with endogenous peroxidase activity by contacting them with an appropriate peroxidase indicator; and (iv) counting the peroxidase-negative gold-labeled cells in a given sample under the light microscope.

8. The method of claim 6 wherein said subpopulation of human T-lymphocytes is the helper/inducer subpopulation.

9. The method of claim 6 wherein said subpopulation of human T-lymphocytes is the suppressor/cytotoxic subpopulation.

10. The method of claim 7 wherein said subpopulation of human T-lymphocytes is the helper/inducer subpopulation.

11. The method of claim 7 wherein said subpopulation of human T-lymphocytes is the suppressor/cytotoxic subpopulation.

12. A bright field light microscopic method for the quantitative determination of human monocytes which comprises the steps of (i) labeling said monocytes by allowing them to react, in a viable state, with gold-labeled antibodies to human monocytes, whereby the cells are, until fixation, allowed to undergo extensive patching of the antigens, but are prevented from capping and all forms of internalization by keeping them in contact with an effective concentration of an appropriate inhibitor of oxidative phosphorylation;

(ii) fixing the cells and staining the cells with endogenous peroxidase activity by contacting them with an appropriate peroxidase indicator; and (iii) counting the peroxidase-positive gold-labeled cells in a given sample under the light microscope.

13. A bright field light microscopic method for the quantitative determination of human monocytes which comprises the steps of (i) allowing said monocytes to react, in a viable state, with non-labeled antibodies to human monocytes;

(ii) labeling the thus formed complexes by allowing them to react with appropriate gold-labeled secondary antibodies, whereby the cells are, until fixation, allowed to undergo extensive patching of the antigens, but are prevented from capping and all forms of internalization by keeping them in contact with an effective concentration of an appropriate inhibitor of oxidative phosphorylation;

(iii) fixing the cells and staining the cells with endogenous peroxidase activity by contacting them with an appropriate peroxidase indicator; and (iv) counting the peroxidase-positive gold-labeled cells in a given sample under the light microscope.

14. The method of claim 6 wherein said inhibitor of oxidative phosphorylation is sodium azide.

15. The method of claim 7 wherein said inhibitor of oxidative phosphorylation is sodium azide.

16. The method of claim 8 wherein said inhibitor of oxidative phosphorylation is sodium azide.

17. The method of claim 9 wherein said inhibitor of oxidative phosphorylation is sodium azide.

18. The method of claim 10 wherein said inhibitor of oxidative phosphorylation is sodium azide.

19. The method of claim 11 wherein said inhibitor of oxidative phosphorylation is sodium azide.

* * * * *